United States Patent

Starner et al.

[11] Patent Number: 5,202,001
[45] Date of Patent: * Apr. 13, 1993

[54] PREPARATION OF URETHANE PREPOLYMERS HAVING LOW LEVELS OF RESIDUAL TOLUENE DIISOCYANATE

[75] Inventors: William E. Starner, Nesquehoning; Bernard A. Toseland; Reinaldo M. Machado, both of Allentown, all of Pa.; Albert J. Siuta, Sewell, N.J.

[73] Assignee: Air Products and Chemicals, Inc., Allentown, Pa.

[*] Notice: The portion of the term of this patent subsequent to Sep. 24, 2008 has been disclaimed.

[21] Appl. No.: 727,501

[22] Filed: Jul. 9, 1991

Related U.S. Application Data

[63] Continuation-in-part of Ser. No. 412,953, Sep. 26, 1989, Pat. No. 5,051,152.

[51] Int. Cl.$^5$ .................. B01D 1/00; B01D 3/00
[52] U.S. Cl. ........................ 203/49; 159/6.2; 159/16.1; 159/49; 159/DIG. 10; 203/89; 560/352
[58] Field of Search ............ 203/49, 89, 98, 91; 159/49, 6.2, 16.1, 901, DIG. 10; 202/236; 560/352

[56] References Cited

U.S. PATENT DOCUMENTS

| | | | |
|---|---|---|---|
| 3,183,112 | 5/1965 | Gemassmer | 106/316 |
| 3,248,372 | 4/1966 | Bunge | 528/53 |
| 3,384,624 | 5/1968 | Helss | 528/49 |
| 3,516,950 | 6/1970 | Haggis | 521/112 |
| 3,549,504 | 12/1970 | Adica et al. | 203/49 |
| 3,843,936 | 12/1974 | Van Winkle | 203/99 |
| 3,883,522 | 5/1975 | Rabizzoni | 560/26 |
| 3,912,600 | 10/1975 | Hatfield | 203/88 |
| 4,061,662 | 12/1977 | Marans et al. | 560/26 |
| 4,216,063 | 8/1980 | Ailloud et al. | 159/6.2 |
| 4,294,666 | 10/1981 | Astheimer et al. | 560/352 |
| 4,338,408 | 7/1982 | Zimmerman et al. | 521/167 |
| 4,385,171 | 5/1983 | Schnabel et al. | 528/491 |
| 4,683,279 | 7/1987 | Milligan et al. | 528/67 |
| 4,786,703 | 11/1988 | Starner et al. | 538/63 |
| 4,853,419 | 8/1989 | Hallmark et al. | 521/172 |
| 5,051,152 | 9/1991 | Siuta et al. | 203/89 |

OTHER PUBLICATIONS

Kirk–Othmer Encyclopedia of Chemical Technology, Third Edition vol. 9 Enamels, Porcelain or Vitreous B Ferrites pp. 478–481.

Primary Examiner—Virginia Manoharan
Attorney, Agent, or Firm—Michael Leach; James C. Simmons; William F. Marsh

[57] ABSTRACT

A wiped film evaporation process for reducing the amount of residual organic polyisocyanate, especially toluene diisocyanate, in a polyurethane prepolymer reaction product mixture. An inert sweeping gas is added to the evaporation process, preferably after first passing through a holdup volume of the prepolymer which has passed through the evaporation zone.

15 Claims, No Drawings

PREPARATION OF URETHANE PREPOLYMERS HAVING LOW LEVELS OF RESIDUAL TOLUENE DIISOCYANATE

CROSS-REFERENCE TO RELATED APPLICATIONS

The present application is a continuation-in-part of U.S. application Ser. No. 07/412,953, filed Sep. 26, 1989, now U.S. Pat. No. 5,051,152.

TECHNICAL FIELD

The present invention relates to a process for removing monomeric polyisocyanate from polyurethane prepolymers and, more particularly, relates to an evaporative process for such removal.

BACKGROUND OF THE INVENTION

Polyurethane prepolymers obtained by reacting an organic diisocyanate with a polyol are commonly used in industry to make a wide variety of cellular and noncellular polyurethane products. In preparing the prepolymer a stoichiometric excess of diisocyanate (i.e., an equivalent NCO/OH ratio of greater than 2/1) is generally employed. However, the use of such a relative proportion of the reactants leads to an increase in the amount of unreacted diisocyanate in the prepolymer reaction product. This has been found to be undesirable because diisocyanate vapors are believed to be toxic to humans and may pose a health hazard to workers exposed to high diisocyanate levels over an extended period of time.

A number of processes have been developed in an effort to reduce the unreacted diisocyanate content in polyurethane prepolymers:

U.S. Pat. No. 3,183,112 discloses a method for removing unreacted diisocyanate from the reaction mixture of an excess of organic diisocyanate with a polyol after reaction has ceased which comprises flowing the reaction mixture as a thin film and heating the film at a temperature of 150° C. or more while agitating the film of the reaction mixture to avoid any quiescence. The apparatus used is a falling film evaporator. It is stated to be advantageous to flush the evaporator by pumping a suitable solvent into the bottom thereof to aid in removing the isocyanate vapor therefrom. Example 5 shows about 0.02 parts o-dichlorobenzene vapor per one part polyisocyanate is pumped into the bottom of the evaporator to flush out the polyisocyanate vapors.

U.S. Pat. No. 3,248,372 discloses a method for polymerizing an organic polyisocyanate to form a polymer having unreacted-NCO groups wherein a monomeric organic diisocyanate is reacted with a glycol and the resulting urethane diisocyanate is heated under alkaline conditions until a polymeric organic polyisocyanate soluble in organic solvents conventionally used in making lacquers and containing less than about 1% of the monomer in admixture therewith is obtained. The excess organic diisocyanate can be separated from the resulting urethane diisocyanate by subjecting the mixture to a vacuum treatment or a single extraction with a solvent.

U.S. Pat. No. 3,384,624 discloses that monomeric toluene diisocyanate (TDI) is removed from a prepolymer composition by reacting the monomeric TDI remaining in the prepolymer with a benzyl alcohol.

U.S. Pat. No. 3,883,577 discloses a process for producing high molecular weight polyisocyanates using, as solvent medium for the reaction between the volatile diisocyanate and hydrogen containing substance, a solvent, in particular acetonitrile, which has a strong affinity for the high molecular weight polyisocyanate, is only partially miscible with the aliphatic and/or cycloaliphatic hydrocarbons used as solvent for the extraction of unreacted volatile isocyanate, has a low boiling point by virtue of which it is easily distillable without causing collateral reactions and, finally, may be replaced by the solvents which are normally used in applying the high molecular weight polyisocyanates in practice.

U.S. Pat. No. 4,061,662 discloses a process for removing unreacted TDI from a polyisocyanate by bringing the polyisocyanate into contact with molecular sieves.

U.S. Pat. No. 4,385,171 discloses that unreacted diisocyanate is removed from the polyurethane prepolymer reaction product mixture by co-distillation of the unreacted diisocyanate with a compound which is at least partially miscible with the prepolymer and which boils at a temperature greater than the boiling point of the diisocyanate.

U.S. Pat. No. 4,683,279 discloses urethane linked mixtures of 2,4- and 2,6-toluene diisocyanates (ULTDI dimers) having low melting points. After the reaction of TDI with the preselected polyol, excess isocyanate may be removed from the reaction product by distillation. Example 1 discloses that the product was recovered by distilling at 100° C. and 0.1 mm Hg in a wiped film apparatus to remove unreacted toluene diisocyanate.

SUMMARY OF THE INVENTION

The present invention is an improvement in a evaporative process, or distillation, for reducing the amount of residual polyisocyanate in a polyurethane prepolymer reaction product mixture in which the prepolymer is prepared by reacting an organic polyisocyanate with a polyol. An inert gas is added to the distillation process, preferably using a film-type evaporator, to sweep out the polyisocyanate.

As advantages of the addition of the inert gas, the distillation rate is increased by increasing the driving force, the equilibrium level of polyisocyanate in the prepolymer product is lowered at a given temperature, and the distillation process can be performed at lower temperatures. The diisocyanate content of the polyurethane prepolymer can be reduced below 0.1 wt % on a commercial scale.

In a preferred embodiment the inert gas that is added to the evaporator is first passed through a holdup volume of the liquid prepolymer that has passed through the evaporator.

DETAILED DESCRIPTION OF THE INVENTION

According to the present invention, an improved removal of residual diisocyanate from polyurethane prepolymers can be achieved. In practicing the process of the present invention, residual diisocyanate is distilled from the prepolymer reaction product mixture while an inert sweeping gas is passed through the distillation apparatus. The residual diisocyanate content in the prepolymer mixture can be reduced to less than 0.1 wt %.

The polyurethane prepolymer that is used according to the present invention is prepared by reacting an organic diisocyanate with a polyol using standard procedures known in the art. In carrying out the reaction, it is preferred that the NCO/OH equivalent ratio be in excess of about 2/1.

Suitable organic diisocyanates include toluene diisocyanate (TDI), such as the 80:20 and the 65:35 mixtures of the 2,4- and 2,6-isomers, ethylene diisocyanate, propylene diisocyanate, methylene-bis[(4-phenyl)isocyanate] (MDI), methylene-bis[(4-cyclohexyl)isocyanate] (CHDI), xylene diisocyanate, hexamethylene diisocyanate, isophorone diisocyanate and the like and mixtures thereof. It is preferred to use an isomeric mixture of 2,4- and 2,6-TDI in which the weight ratio of the 2,4-isomer to the 2,6-isomer is from about 45:55 to about 90:10, and more preferably from about 65:35 to about 80:20 for typical polyurethane prepolymers.

The polyol reactant used in the polyurethane prepolymer formation may be a polyether polyol, a polyester polyol or a mixture of two or more of such compounds. The polyol, or mixture of polyols, preferably has a molecular weight from about 62 to about 7,000. The average functionality of the polyol or polyol blend is usually about 2 to about 8, and preferably about 2 to about 4.

The polyester polyols include the products of reacting polycarboxylic acids or anhydrides with polyhydric alcohols including various diols, triols, tetrols and higher functionality alcohols. Suitable polyether polyols include various polyoxyalkylene polyols and mixtures thereof. These can be prepared, according to well known methods, by condensing an alkylene oxide, or a mixture of alkylene oxides using random or step-wise addition, with a polyhydric initiator or a mixture of initiators. Illustrative alkylene oxides include ethylene oxide, propylene oxide, and butylene oxide.

In a particularly preferred embodiment, residual TDI is removed from urethane linked toluene diisocyanates containing from 45-90% of the 2,4- and 10-55% of the 2,6-isomer by weight which are formed by reacting 2 moles of an appropriate isomer mix of TDI with one mole of a specific alkylene glycol as disclosed in U.S. Pat. No. 4,683,279.

The distillation process of the invention is preferably performed by subjecting the crude prepolymer reaction product mixture derived from the reaction between the organic polyisocyanate and the polyol to distillation in a wiped film evaporator, preferably after an initial pass through the evaporator without an inert gas flow. An inert gas, such as nitrogen, helium, dry air or halocarbons is added to and passed through the distillation, preferably in a countercurrent flow and on the second pass of the prepolymer through the evaporator, to facilitate removal of the residual diisocyanate. The flow rate of the inert gas into the distillation process is such that the ratio of the inert gas mass flow rate to the diisocyanate-containing prepolymer mass flow rate is greater than about 0.06 (mol wt inert gas/mol wt diisocyanate) and less than about 1.55 (mol wt inert gas/mol wt diisocyanate), although the upper limit may be as high as practical for the vacuum system:

$$0.06 \left( \frac{\text{mol wt gas}}{\text{mol wt di-NCO}} \right) < \frac{\text{mass flow rate gas}}{\text{mass flow rate prepolymer}} < 1.55 \left( \frac{\text{mol wt gas}}{\text{mol wt di-NCO}} \right)$$

Preferably the ratio of the inert gas mass flow rate to the prepolymer mass flow rate is as follows:

$$0.3 \left( \frac{\text{mol wt gas}}{\text{mol wt di-NCO}} \right) < \frac{\text{mass flow rate gas}}{\text{mass flow rate prepolymer}} < 1 \left( \frac{\text{mol wt gas}}{\text{mol wt di-NCO}} \right)$$

In general, the distillation process is carried out in a conventional manner, the actual conditions being dependent upon the diisocyanate being removed, the other components of the distillation mixture and the like. (Suitable film-type evaporators, including falling film and wiped film evaporators, are disclosed in Kirk-Othmer, *Encyclopedia of Chemical Technology*, Third Edition, vol. 9, pp. 478-481). Usually, however, the distillation temperature ranges from about 80° C. to about 225° C., preferably from about 100° C. to about 160° C. The distillation pressure will typically range from about 0.03 to about 10 mm Hg, with a pressure of about 0.5 to about 5 mm Hg being preferred.

In the most desirable embodiment, the inert gas is first passed through a holdup volume of prepolymer that has passed through the evaporation zone.

The limits on distillation are both temperature and residence time. Both can lead to poor product quality because of product degradation. Too low a distillation temperature or too high a pressure will leave TDI in the prepolymer product. Thus, high temperatures are inherent in distillation. However, heavy materials, i.e. oligomers, are formed at higher temperatures. On the other hand, allophanates are formed when the prepolymer reaction mixture is allowed to sit at lower temperatures. (Both allophanates and oligomers are identified by a drop in the % NCO). Thus, simple distillation in which the material sits in the reboiler of the column and decomposes or an increase in the temperature of a wiped film evaporator results in lower product quality.

The addition of the inert gas to the distillation lowers the equilibrium concentration of the TDI (increases TDI removal) and reduces the boiling temperature of the distillate.

It has been discovered that the prepolymer will decompose at high temperatures yielding TDI as one of the products of the decomposition. Thus, attempts to distill TDI from the polymer reaction product are frustrated by making TDI during distillation process. This formation of TDI limits conventional distillation and wiped film evaporators in removing TDI.

The present process balances the need for putting in heat (necessarily at temperatures near the decomposition point) to effect a desired separation and the decomposition of the material. (Decomposition has two effects, namely decreasing the product quality and generating the very substance to be removed.) The use of inert gas allows a lower temperature of distillation at the same level of TDI by reducing the equilibrium TDI concentration for a given temperature. Addition of the inert gas also causes an increase in the driving force for mass transfer resulting in a shorter residence time. In addition, purging a holdup volume of prepolymer which has passed through the distillation zone with an inert gas stream, i.e., post-stripping, further removes TDI which may have been formed by the heating of the prepolymer in the evaporator.

The following examples are provided to further illustrate the invention. All parts are by weight unless otherwise specified. TDI polyurethane polymer reaction mixtures used in the following examples were prepared in conventional fashion according to U.S. Pat. No. 4,683,779.

EXAMPLE 1

Runs 1-9 used TDI prepolymer reaction product mixtures differing only in the molecular weight of the polyol used in their preparation. In all the Runs, nitrogen was used as the sweeping gas. The distillations were preformed using a Pope 2-inch wiped film still. The feed rate was controlled by passing the feed through a capillary tube of the correct size. The feed rates varied slightly with time. The product rates set forth in Table 1 are an average over the run length (4-26 hours). A new batch of feed was prepared for each Run. Thus, the initial TDI content varied slightly between the cases with and without inert gas. This variation is not significant since the amount of TDI to be removed is relatively large and the initial removal down to 3-4% is accomplished rapidly with little difficulty.

TABLE 1

| Run | 1 | 2 | 3 | 4 | 5 | 6 | 7 | 8 | 9 |
|---|---|---|---|---|---|---|---|---|---|
| Prepolymer Mol. Wt. | 1364 | 1364 | 1022 | 1022 | 1022 | 2377 | 2377 | 2377 | 2377 |
| $N_2$ Flow (g/min) | 0 | 0.236 | 0 | 0.184 | 0.179 | 0 | 0.176 | 0.236 | 0.177 |
| Pressure (mm Hg) | 0.18 | 2 | 0.5 | 2 | 2 | 0.12 | 2 | 3 | 2 |
| Temperature (°C.) | 100 | 100 | 100 | 100 | 78 | 100 | 110 | 110 | 110 |
| TDI in Feed (wt %) | 43.2 | 57.5 | 50.6 | 49.4 | 49.4 | 29.4 | 29.4 | 29.4 | 29.4 |
| TDI in Product (wt %) | 0.144 | 0.076 | 0.39 | 0.054 | 0.085 | 0.181 | 0.0067 | 0.118 | 0.0056 |
| Product Flow Rate (g/hr) | 58.4 | 96.1 | 135 | 129 | 142 | 36.8 | 18 | 17.2 | 19.3 |
| % NCO Theoretical | 6.2 | 6.2 | 8.22 | 8.22 | 8.22 | 3.53 | 3.53 | 3.53 | 3.53 |
| % NCO Out | — | 6.35 | 8.4 | 8.33 | — | 3.65 | 3.71 | 3.69 | 3.72 |

It can be seen from the data in Table 1 that for the three prepolymers of different molecular weight, nitrogen was effective at lowering the residual TDI level to about 0.1 wt % compared to Runs 1, 3 and 6 in which no nitrogen was used. Run 3 also shows that increasing the pressure in the evaporator leads to a higher TDI concentration in the product.

EXAMPLE 2

In this Example Runs 10 and 11 show the effectiveness of using nitrogen as a stripping gas to reduce residual TDI levels below 0.1 wt %. The Runs were performed on a Pfaudler high vacuum unit with an internal condenser. The system was placed under vacuum using a five stage steam ejector system. The jacket temperature was controlled using hot oil. The feed was started and the rate controlled using a metering pump. Samples were drawn continuously off the discharge of the residue pump.

| Run | 10 | 11 | 12 | 13 |
|---|---|---|---|---|
| Polymer Mol. Wt. | 1000 | 1000 | 1338 | 1338 |
| Nitrogen Flow (lbs/hr) | 0 | 2.1 | 0 | 2.0 |
| Jacket Temp. (°C.) | 204 | 204 | 201 | 201 |
| Evaporator Pres. (mm Hg abs) | 0.74 | 0.74 | 0.66 | 0.68 |
| TDI in Feed (wt %) | 13.7 | 13.7 | 5.3 | 5.3 |
| TDI in Residue (wt %) | 0.13 | 0.06 | 0.16 | 0.08 |
| Feed Rate (lbs/hr) | 69.5 | 69.5 | 45.0 | 49.0 |

EXAMPLE 3

This example shows the best residual TDI levels obtained when the evaporation was performed at extremely low pressures without nitrogen sweep. Runs 14-16 were performed on a 4 ft$^2$ Luwa SAMVAC unit with an internal condenser. The vacuum was achieved using a combination vacuum pump and steam ejector system. The jacket was heated using hot oil.

| Run | 14 | 15 | 16 |
|---|---|---|---|
| Polymer Mol. Wt. | 540 | 540 | 540 |
| Nitrogen Flow (lbs/hr) | 0 | 0 | 0 |
| Jacket Temp. (°C.) | 180 | 200 | 255 |
| Evaporator Pres. (mm Hg absx) | 0.06 | 0.04 | 0.04 |
| TDI in Feed (wt %) | 16.7 | 16.7 | 16.7 |
| TDI in Residue (wt %) | 0.36 | 0.20 | 5.0 |
| Feed Rate (lbs/hr) | 52.5 | 52.5 | 56.3 |

The lowest level of residual TDI was 0.2 wt % in Run 15. The residual TDI level rose dramatically in Run 16 when the jacket temperature was increased to 255° C. This was believed due to thermal degradation of the prepolymer to form free TDI.

EXAMPLE 4

Runs 17-20 show the residual TDI levels achieved during wiped film evaporation with a nitrogen stripping gas. All runs were made on a Pfaudler wiped film evaporator with an internal condenser.

| Run | 17 | 18 | 19 | 20 |
|---|---|---|---|---|
| Polymer Mol. Wt. | 540 | 1000 | 1338 | 2298 |
| Nitrogen Flow (lbs/hr) | 1.6 | 2.1 | 1.4 | 1.5 |
| Jacket Temp. (°C.) | 160 | 141 | 141 | 161 |
| Evaporator Pres. (mm Hg absx) | 1.30 | 0.79 | 0.60 | 0.73 |
| TDI in Feed (wt %) | 22.2 | 13.7 | 8.8 | 5.6 |
| TDI in Residue (wt %) | 0.06 | 0.06 | 0.06 | 0.02 |
| Feed Rate (lbs/hr) | 55.3 | 46.3 | 57.6 | 50.8 |

EXAMPLE 5

In this experiment Runs 21-23 were performed on a Pfaudler wiped film evaporator with an internal condenser. The jacket temperature was controlled using hot oil. The five stage steam ejector system was used to reduce the operating pressure. The location for adding the nitrogen stripping gas was varied in each run.

| Run | 21 | 22 | 23 |
| --- | --- | --- | --- |
| Polymer Mol. Wt. | 2298 | 2298 | 2298 |
| Nitrogen Flow (lbs/hr) | — | — | — |
| To Top Head | 1.6 | 0.6 | 0 |
| To Residue Line | 1.4 | 1.5 | 1.5 |
| Jacket Temp. (°C.) | 142 | 142 | 142 |
| Evaporator Pres. (mm Hg absx) | 1.15 | 0.90 | 0.89 |
| TDI in Feed (wt %) | 5.6 | 5.6 | 5.6 |
| TDI in Residue (wt %) | 0.10 | 0.11 | 0.07 |
| Feed Rate (lbs/hr) | 40.2 | 52.9 | 50.8 |

It can be seen from the data that the addition of the nitrogen stripping gas to the residue line, i.e., countercurrent stripping, provided the lowest level of TDI in the product.

EXAMPLE 6

In this example, a ball valve was inserted into the evaporator residue line above the nitrogen inlet of the wiped film evaporator used in Example 5.

| Run | 24 | 25 |
| --- | --- | --- |
| Polymer Mol. Wt. | 1338 | 1338 |
| Nitrogen Flow (lbs/hr) | 3.0 | 3.0 |
| Jacket Temp. (°C.) | 150 | 150 |
| Evaporator Pres. (mm Hg absx) | 2.0 | 2.0 |
| TDI in Feed (wt %) | 7.2 | 7.2 |
| TDI in Residue (wt %) | 0.36 | 0.16 |
| Feed Rate (lbs/hr) | 32 | 32 |
| Ball Valve Position: | Fully Open (No Liquid Holdup) | Partially Closed (Liquid Holdup) |

It can be seen that a marked improvement in TDI removal was achieved when the ball valve was partially closed in Run 25. The ball valve provided better mixing of the gas and liquid phases by creating a liquid-holdup when it was closed partially during the evaporation run. Samples collected with the ball valve partially closed showed entrained gas bubbles. These bubbles are indicative of better vapor-liquid contacting and an increased area for mass transfer.

EXAMPLE 7

This example demonstrates the improvement of the inventive method for removing isophorone diisocyanate (IPDI) from a prepolymer reaction mixture using dry air as the sweeping gas in a wiped film evaporator.

A prepolymer was synthesized from IPDI and a 1000 molecular weight poly(tetramethylene oxide)glycol (PTMEG) at a 10:1 NCO:OH ratio. A jacketed reactor equipped with a nitrogen purge and a mechanical stirrer was first charged with 6681.3 g IPDI (eq wt 111.15) and heated to 80° C. Next 2933.2 g of PTMEG-1000 (DuPont Terathane 1000) OH#114.8 (eq wt 488.7) were added slowly to the reactor over 2.5 h with rapid stirring. The reaction mixture was held for an additional 18 h at 80° C. after the polyol addition was completed.

The IPDI/PTMEG-1000 prepolymer was distilled on a 1.2 sq ft wiped film evaporator (Pope Scientific) using the following distillation conditions:

| Feed Rate | 19.9 g/min |
| --- | --- |
| WFE Jacket Temperature | 175° C. |
| WFE Condenser Temperature | 10° C. |
| Vacuum Pressure | 1.0 Torr |
| Feed Temperature | Ambient |
| Dry Air Flow | 0.1 SLPM |

After first contacting a hold-up volume of prepolymer reaction mixture that had passed through the evaporator, zero grade air (Air Products), a synthetic blend of oxygen and nitrogen, was used as the stripping agent at a flow rate of 0.1 SLPM. The system was allowed to equilibrate under these operating conditions for about one hour. A sample was then taken over a period of 30 minutes. The analysis of that sample by HPLC-RI indicated 0.09% residual IPDI remained in the sample.

The dry air flow was then shut off with all of the above conditions remaining the same:

| Feed Rate | 20.1 g/min |
| --- | --- |
| WFE Jacket Temperature | 175° C. |
| WFE Condenser Temperature | 10° C. |
| Vacuum Pressure | 1.0 Torr |
| Feed Temperature | Ambient |
| Dry Air Flow | 0 SLPM |

The distillation was allowed to equilibrate for one hour and then a sample was taken over 30 minutes. The analysis of the second sample by HPLC-RI indicated 0.18% IPDI remained in the sample. Thus, this example shows the improvement in reducing residual IPDI levels using dry air as the inert sweeping gas.

EXAMPLE 8

This example demonstrates reducing the residual level of methylene-bis[(4-cyclohexyl)diisocyanate] (CHDI) in a prepolymer reaction mixture using helium as the sweeping gas in a wiped film evaporator.

A prepolymer was synthesized from CHDI (Mobay Desmodur W) and a 1000 molecular weight poly(tetramethylene oxide)glycol (PTMEG) at a 10:1 NCO:OH ratio. A jacketed reactor equipped with a nitrogen purge and a mechanical stirrer was first charged with 8201.3 g CHDI (eq wt 131) and heated to 80° C. Next 3052.5 g of PTMEG-1000 (DuPont Terathane 1000) OH#114.8 (eq wt 488.7) were added slowly to the reactor over 2.5 h with rapid stirring. The reaction mixture was held for an additional 16.5 h at 80° C. after the polyol addition was completed.

The CHDI/PTMEG-1000 prepolymer was distilled on a 1.2 sq ft wiped film evaporator (Pope Scientific) using the following distillation conditions:

| Feed Rate | 8.4 g/min. |
| --- | --- |
| WFE Jacket Temperature | 200° C. |
| WFE Condenser Temperature | 10° C. |
| Vacuum Pressure | 0.9 Torr |
| Feed Temperature | Ambient |
| Helium Flow | 0.1 SLPM |

After first contacting a hold-up volume of prepolymer reaction mixture that had passed through the evaporator, zero grade helium (Air Products) was used as the stripping agent at a flow rate of 0.1 SLPM in countercurrent flow to the prepolymer reaction mixture. The system was allowed to equilibrate under these operating conditions for about 1 hour. A sample was then taken over a period of 30 minutes. The analysis of that sample by SFE-GC indicated 0.04% residual CHDI remained in the sample.

The helium flow was then shut off with all of the above conditions remaining the same:

| | |
|---|---|
| Feed Rate | 8.4 g/min. |
| WFE Jacket Temperature | 200° C. |
| WFE Condenser Temperature | 10° C. |
| Vacuum Pressure | 0.9 Torr |
| Feed Temperature | Ambient |
| Helium Flow | 0 SLPM |

The distillation was allowed to equilibrate for one hour, and then a sample was taken over 30 minutes. The analysis of the second sample by SFE-GC indicated 0.37% CHDI remained in the sample. Thus, this example shows the great improvement in reducing residual CHDI levels using helium as the inert sweeping gas.

STATEMENT OF INDUSTRIAL APPLICATION

The present distillation process provides a method for obtaining polyurethane prepolymers containing very low levels of residual organic polyisocyanate.

We claim:

1. In a process for reducing the amount of residual organic diisocyanate ("di-NCO") in a polyurethane prepolymer reaction product mixture which comprises passing the prepolymer reaction product mixture through a wiped film evaporation zone, the improvement which consists essentially of passing an inert gas through a quantity of the prepolymer which has passed through the evaporation zone and passing the inert gas in a countercurrent flow through the evaporation zone such that $$0.06 \left( \frac{\text{mol wt gas}}{\text{mol wt di-NCO}} \right) < \frac{\text{mass flow rate inert gas}}{\text{mass flow rate prepolymer}} < 1.55 \left( \frac{\text{mol wt gas}}{\text{mol wt di-NCO}} \right)$$

to provide a resulting prepolymer product which contains less than about 0.1 wt % residual organic diisocyanate.

2. The process of claim 1 in which the inert gas is nitrogen.

3. The process of claim 1 in which the inert gas is dry air.

4. The process of claim 1 in which the inert gas is helium.

5. The process of claim 1 in which the organic diisocyanate is 2,4-toluene diisocyanate, 2,6-diisocyanate or mixture thereof.

6. The process of claim 1 in which the organic diisocyanate is methylene-bis[(4-cyclohexyl)isocyanate].

7. The process of claim 1 in which the organic diisocyanate is isophorone diisocyanate.

8. In a process for reducing the amount of residual organic diisocyanate ("di-NCO") in a polyurethane prepolymer reaction product mixture, the organic diisocyanate being selected from the group consisting of toluene diisocyanate, methylene-bis[(4-cyclohexyl)isocyanate] and isophorone diisocyanate, which comprises passing the prepolymer reaction product mixture through a wiped film evaporation zone, the improvement which consists essentially of passing an inert gas selected from the group consisting of nitrogen, dry air and helium through a quantity of the prepolymer which has passed through the evaporation zone and passing the inert gas in a countercurrent flow through the evaporation zone such that $$0.06 \left( \frac{\text{mol wt gas}}{\text{mol wt di-NCO}} \right) < \frac{\text{mass flow rate inert gas}}{\text{mass flow rate prepolymer}} < 1.55 \left( \frac{\text{mol wt gas}}{\text{mol wt di-NCO}} \right)$$

to provide a resulting prepolymer product which contains less than about 0.1 wt % residual organic diisocyanate.

9. In a process for reducing the amount of residual organic diisocyanate ("di-NCO") in a polyurethane prepolymer reaction product mixture which comprises passing the prepolymer reaction product mixture through a wiped film evaporation zone, the improvement which consists essentially of passing an inert gas through the evaporation zone and passing the inert gas in a countercurrent flow through the evaporation zone such that $$0.3 \left( \frac{\text{mol wt gas}}{\text{mol wt di-NCO}} \right) < \frac{\text{mass flow rate inert gas}}{\text{mass flow rate prepolymer}} < 1 \left( \frac{\text{mol wt gas}}{\text{mol wt di-NCO}} \right)$$

to provide a resulting prepolymer product which contains less than about 0.1 wt % residual organic diisocyanate.

10. The process of claim 9 in which the inert gas is nitrogen.

11. The process of claim 9 in which the inert gas is dry air.

12. The process of claim 9 in which the inert gas is helium.

13. The process of claim 9 in which the organic diisocyanate is 2,4-toluene diisocyanate, 2,6-toluene diisocyanate or a mixture thereof.

14. The process of claim 9 in which the organic diisocyanate is methylene-bis[(4-cyclohexyl)isocyanate].

15. The process of claim 9 in which the organic diisocyanate is isophorone diisocyanate.

* * * * *